(12) United States Patent
Valdesuso Aguilar et al.

(10) Patent No.: US 9,186,265 B2
(45) Date of Patent: Nov. 17, 2015

(54) IMPLANTABLE MEDICAL DEVICE HAVING A MEANS FOR POSITIONING IT AT THE PRECISE SITE OF A BRANCHING OF A BLOOD VESSEL SUCH AS A CORONARY ARTERY

(75) Inventors: Raul M. Valdesuso Aguilar, Alicante (ES); Gilles Ascher, Neuilly-sur-Seine (FR)

(73) Assignee: HEXACATH, Rueil-Malmaison (FR)

( * ) Notice: Subject to any disclaimer, the term of this patent is extended or adjusted under 35 U.S.C. 154(b) by 422 days.

(21) Appl. No.: 12/992,244

(22) PCT Filed: May 12, 2009

(86) PCT No.: PCT/FR2009/050870
§ 371 (c)(1),
(2), (4) Date: Jun. 30, 2011

(87) PCT Pub. No.: WO2009/147349
PCT Pub. Date: Dec. 10, 2009

(65) Prior Publication Data
US 2011/0264189 A1   Oct. 27, 2011

(30) Foreign Application Priority Data

May 12, 2008  (FR) ..................................... 08 53064

(51) Int. Cl.
| A61F 2/06 | (2013.01) |
| A61F 2/91 | (2013.01) |
| A61F 2/958 | (2013.01) |
| A61F 2/82 | (2013.01) |

(52) U.S. Cl.
CPC . *A61F 2/91* (2013.01); *A61F 2/958* (2013.01); *A61F 2002/061* (2013.01); *A61F 2002/821* (2013.01); *A61F 2230/0054* (2013.01)

(58) Field of Classification Search
CPC ............. A61F 2/82; A61F 2/856; A61F 2/86; A61F 2/954; A61F 2/958
USPC ........... 623/1.11, 1.34, 1.35, 1.12, 1.13, 1.14, 623/1.15, 1.23, 1.16, 1.17, 1.18, 1.19; 606/194, 198
See application file for complete search history.

(56) References Cited

U.S. PATENT DOCUMENTS

| 6,221,090 B1 * | 4/2001 | Wilson .......................... 606/194 |
| 6,736,844 B1 * | 5/2004 | Glatt et al. .................... 623/1.22 |
| 2002/0120323 A1 * | 8/2002 | Thompson et al. ........... 623/1.11 |
| 2002/0188344 A1 * | 12/2002 | Bolea et al. ................... 623/1.11 |

(Continued)

FOREIGN PATENT DOCUMENTS

| FR | 2896982 | 8/2007 |
| WO | 2007-014088 | 2/2007 |
| WO | 2007-025101 | 3/2007 |

*Primary Examiner* — Katrina Stransky
(74) *Attorney, Agent, or Firm* — Lucas & Mercanti, LLP (57) ABSTRACT

The invention relates to an implantable medical device. This implantable medical device (10) to be implanted at an implantation site comprises a proximal end (P), a central portion (C) and a distal end (D), characterized in that it comprises, at its proximal end (P), at least one means (20) for positioning the implantable device (10) at a precise point of a branching (E) of a blood vessel (V), such as a coronary artery. The invention provides precise, exact and almost perfect positioning of the implantable medical device 10 such as a stent 11 at the branching E of the blood vessel V to be treated, in order to treat the ostial lesions or stenoses that have been very difficult to treat until now.

20 Claims, 5 Drawing Sheets

(56) References Cited

U.S. PATENT DOCUMENTS

| | | | |
|---|---|---|---|
| 2002/0193873 A1* | 12/2002 | Brucker et al. | 623/1.35 |
| 2003/0114912 A1* | 6/2003 | Sequin et al. | 623/1.11 |
| 2003/0125791 A1* | 7/2003 | Sequin et al. | 623/1.11 |
| 2003/0135261 A1 | 7/2003 | Kugler et al. | |
| 2003/0149469 A1* | 8/2003 | Wolinsky et al. | 623/1.11 |
| 2003/0176912 A1* | 9/2003 | Chuter et al. | 623/1.13 |
| 2003/0236566 A1* | 12/2003 | Heuser | 623/1.12 |
| 2004/0215329 A1* | 10/2004 | Vonderwalde et al. | 623/1.16 |
| 2005/0096726 A1* | 5/2005 | Sequin et al. | 623/1.12 |
| 2005/0154444 A1* | 7/2005 | Quadri | 623/1.13 |
| 2005/0172471 A1* | 8/2005 | Vietmeier | 29/447 |
| 2006/0190070 A1* | 8/2006 | Dieck et al. | 623/1.12 |
| 2006/0271090 A1 | 11/2006 | Shaked et al. | |
| 2007/0043432 A1* | 2/2007 | Perouse | 623/1.36 |
| 2007/0129733 A1* | 6/2007 | Will et al. | 606/108 |
| 2007/0244547 A1* | 10/2007 | Greenan | 623/1.35 |
| 2007/0299497 A1* | 12/2007 | Shaolian et al. | 623/1.11 |
| 2008/0009932 A1* | 1/2008 | Ta et al. | 623/1.11 |
| 2008/0046072 A1 | 2/2008 | LaBorde et al. | |
| 2008/0132989 A1* | 6/2008 | Snow et al. | 623/1.12 |
| 2008/0177369 A1* | 7/2008 | Will et al. | 623/1.12 |
| 2009/0012599 A1* | 1/2009 | Broome et al. | 623/1.16 |
| 2009/0048656 A1* | 2/2009 | Wen | 623/1.12 |
| 2010/0030324 A1* | 2/2010 | Seguin et al. | 623/1.35 |

* cited by examiner

IMPLANTABLE MEDICAL DEVICE HAVING A MEANS FOR POSITIONING IT AT THE PRECISE SITE OF A BRANCHING OF A BLOOD VESSEL SUCH AS A CORONARY ARTERY

This is a U.S. National Phase Application under 35 U.S.C. 371 of International Application PCT/FR2009/050870, filed on May 12, 2009. This Application claims the priority of French Application No. 0853064, filed May 12, 2008, the entire contents of both Applications are hereby incorporated by reference.

The invention relates essentially to an implantable medical device comprising, at its proximal end, a means of positioning at a precise point of branching of a blood vessel such as an artery, in particular a coronary artery.

According to a particular embodiment, the invention relates to an implantable device comprising, or in the form of, a stent or an endoprosthesis.

STATE OF THE ART

The stents are well known implantable devices, more commonly called endoprostheses, the purpose of which is to treat lesions in ducts of the human or animal body, more particularly narrowed ducts in human or animal bodies such as a blood vessel, for example an artery, by keeping them open.

These stents or endoprostheses are devices having the appearance of metallic netting conforming to a design and most commonly consist of an alloy of medical steel 316L type, or even of an alloy compatible with an implantation in the human or animal body, for example of nitinol, of a cobalt-based metal or a cobalt-based alloy. It may be presented crimped onto a delivery system called an inflatable dilating catheter making it possible to introduce the implantable device into the vascular system as far as the lesion of the blood vessel, for example a coronary artery to be treated, then to deploy it to implant it firmly in the vessel and keep the latter open by a mechanical action. The device comprising a stent may also be presented in the form of a structure with shape memory (for example made of nitinol), which is implanted by removing the outer sheath of the delivery catheter or guide catheter, which then makes it possible for the stent to be deployed and be impacted against the vascular wall, following a push action and with a view to releasing it from its sheath.

Most coronary lesions are situated in the middle of an arterial segment and fitting the endoprosthesis then presents no major difficulties.

There are, however, other types of arterial lesions, situated on an ostium or else that may be an ostial lesion, that are far more complex to treat.

Ostium is the name given to the start of the vessel, that is to say, to its origin or its branching point. This type of lesion is currently treated using stents that have a non-dedicated conventional design. In this case, the clinician must implant the prosthesis as precisely as possible to cover all of the coronary lesion situated on the ostium while making every attempt to avoid having the stent overlap either upstream or downstream of the lesion and therefore of the ostium. In this type of indication, the stent is often positioned too far upstream or too far downstream of the ostium, which presents the drawback of having either a metal part of the stent situated in the arterial circulation upstream and not implanted in the coronary artery, then presenting a risk of thrombosis for the patient, or the stent positioned too far downstream and not fully covering the ostial coronary lesion, which then presents a risk of restenosis for the patient, the lesion not having all been treated.

To conclude, these days it is relatively complex and often hazardous to treat ostial coronary lesions with coronary endoprostheses with conventional designs.

For examples of implantable devices or endoprostheses such as stents, those skilled in the art can refer, for example, to the document EP-0 969 779 B1; or to EP-A-1 674 117.

The document US 2006/0271090, published 30 Nov. 2006, provides for a catheter system to treat lesions which is appropriate for the treatment of bifurcations. Referring to paragraph 91, page 7 of this document, and also in particular to FIGS. 11a, 11c and 12, it is specified that the implantable medical device 112, such as a stent, is provided with a means 144 of positioning at a precise point of a branching 3 of a blood vessel 1 such as a coronary artery, this auxiliary elongate element 134 being formed by a lateral deviation lumen 136, fixed to the catheter 118 at a fixing point 144. This fixing point 144 is defined as being a "crotch point". It is also specified that, in a particular embodiment, this fixing point 144, at the crotch point, serves to fix the distal end of the lateral branch lumen 136, the latter lumen allowing for the passage of a guide wire which makes it possible to provide a stopping point, see page 7, paragraph 91, the second to last sentence.

In the general description of this document, notably on page 7, paragraph 11, it is specified that the stent has either a dedicated lateral opening or regular openings. With reference to FIGS. 3 to 7, it can be seen that the fixing point 144 has a variable position that may be located toward the middle of the stent.

Because of this, this fixing point, or "crotch point", is situated essentially toward the middle of the catheter or stent, reference 44, and the latter serves to fix the tubular element 40 for the passage of the lateral guide wire 38. It is specified that, when the system is in the vicinity of the bifurcation 3, the branching lateral guide wire 38 is pulled at the proximal end and freed from the distal connection element 46, after which it is advanced into the secondary vessel 2 until the "crotch point" 44 prevents any further advance, following which the balloon 24 is inflated and the stent 12 is deployed, see page 6, paragraph 80, right-hand column, the first four sentences.

This document targets an invention relating to the holder of a stent and does not relate to the stent itself. Because of this, this document represents a technological background relative to the invention described hereinbelow.

Also, the document US 2006/0190070 further provides for a stent comprising, at each end, free meshes 22, see abstract and FIGS. 1A, 1b and 2A.

However, in the context of the bifurcations common to FIGS. 9A and 23C, none of these meshes can be used to precisely position the secondary guide wire.

Because of this, the meshes 22 cannot be used specifically to stop the stent and to guide the secondary guide wire exactly at the point of bifurcation.

Because of this, this document represents a technological background relative to the invention described hereinbelow.

Similarly, the document US 2008/0046072 published 29 Feb. 2008 relates to a bifurcation stent. There are provided, at the proximal end, for certain embodiments, such as the embodiment of FIGS. 23A, 23B, 23C, rings 328, 324 which serve, however, only to support metal markers 330, 326 as results clearly from the description on page 13, paragraph [160] and [161], and paragraph [0165], column 14.

Thus, the meshes 328, 324 do not define an internal orifice, unlike the provisions in the context of the present invention described hereinbelow.

Because of this, this document represents only a technological background relative to the invention.

Moreover, the document WO 2006/085304 discloses a stent which provides extensions 28 to engage the ostium 26 of a secondary vessel 22 as shown in the figures. It obviously emerges from these figures that these extensions 28 are not provided to allow for the passage of a guide or guide wire intended to be implanted in one of the branches of the branching of the blood vessel, unlike the present invention described hereinbelow.

This document therefore also represents a technological background relative to the invention.

Also, the document US 2003/0204240 targets systems of stents for bifurcations at the ventral level. Referring to paragraphs 34 and 35 which refer to FIGS. 1 to 3 and 7, the first embodiment provides an element like a stent 110, called a "cuff", which is combined with a finger-shaped extension 116 which is preferably a nitinol loop, and having a thin layer or wire around it to provide an automatic element to protect the adjacent tissues, see paragraph 35, page 3.

This device as described in FIGS. 1 to 3 is totally different from the invention that emerges from the following description of the invention with reference to the figures.

Finally, the document WO 2007/014088 published by the company Cook, provides a stent comprising a lateral orifice 17 which allows for the passage of a second stent arranged essentially perpendicularly by passing through this lateral orifice 17, see FIGS. 16 to 19.

Thus, the documents of the prior art represent only technological background relative to the invention as described hereinbelow.

AIMS OF THE INVENTION

One main aim of the invention is to resolve the new technical problem consisting in providing an implantable medical device, notably an endoprosthesis or a stent, to treat ducts in the human or animal body, more particularly narrowings of blood ducts in the human or animal body such as a blood vessel, for example an artery, by keeping the ducts open.

Another main aim of the invention is to resolve the new technuique consisting in providing an implantable medical device, notably an endoprosthesis or a stent, to specifically treat ostial coronary lesions safely and reliably.

Another main aim of the invention is to resolve these new technical problems according to a simple solution that is less costly than the previously known implantable devices and that can be used on an industrial and medical scale.

DESCRIPTION OF THE INVENTION

According to a first aspect, the present invention targets an implantable medical device to be implanted at an implantation site comprising a proximal end, a central portion and a distal end, comprising at least at its proximal end or distal end or in its central portion, at least one means for positioning the implantable device at a precise point of a branching of a blood vessel, such as a coronary artery, characterized in that at least one abovementioned positioning means comprises a closed mesh defining an orifice for the passage of a guide or guide wire intended to be introduced into a secondary branch of said branching of the blood vessel, a main branch of which is reached by a stenosis to be treated.

According to the invention, the term "closed mesh" should be understood to mean a mesh that has a continuous contour and that defines a through internal orifice for the passage of a guide wire or guide by preventing it from slipping out of the mesh.

The mesh can be in any form, but its size must be sufficient for the passage of any appropriate guide or guide wire diameter.

According to a particular embodiment of the invention, the abovementioned means of positioning the implantable device comprises at least one closed mesh, of circular or ring shape for example, produced at said proximal end.

According to another particular embodiment of the invention, the abovementioned means of positioning the implantable device comprises at least two closed meshes, for example arranged substantially in diametrically opposite positions, at said proximal end.

According to yet another particular embodiment of the invention, the abovementioned means of positioning the implantable device comprises at least one closed mesh, of circular or ring shape for example, produced at the distal end.

According to a particular variant of this embodiment, the abovementioned means of positioning the implantable device comprises two closed meshes positioned, for example, diametrically opposite, at the distal end.

According to yet another variant embodiment of the invention, the abovementioned means of positioning the implantable device comprises at least one closed mesh defining an orifice for the passage of a guide or guide wire, produced both at the proximal end and at the distal end.

According to a very specific embodiment, the abovementioned device may comprise at least two closed meshes, for example arranged diametrically opposite, at the proximal end and/or at the distal end.

According to yet another particular embodiment of the invention, the abovementioned means of positioning the implantable device comprises at least one closed mesh, or a single closed mesh, for example of circular or ring shape, produced in said central portion and defining an orifice for the passage of a guide or guide wire.

According to yet another particular embodiment of the invention, the abovementioned means of positioning the implantable device may comprise at least one closed mesh, or a single closed mesh, defining an orifice for the passage of a guide or guide wire produced both in the central portion, and at at least one end out of the proximal end and the distal end. At this proximal end and/or at the distal end, there may also be provided at least two closed meshes, for example arranged diametrically opposite.

According to another particular embodiment of the invention, the implantable medical device comprises means for reinforcing the structure, making it possible to exert an action on the proximal and/or distal end and/or its central portion, using a guide or guide wire, without substantial deformation of the implantable medical device.

According to a particular embodiment of the invention, the implantable medical device comprises, or consists of, a stent or endoprosthesis comprising one or more filament-type elements configured with bends or in a zigzag, either in annular turn form or in helical turn form, or a combination of the two. For examples of stents of this type, those skilled in the art can refer to the stent described in the earlier document EP-0 962 779 B1 by at least one of the inventors of the present invention which is formed from one or two filament elements shaped in bends or zigzags comprising, in its proximal end portion, one or more annular or tubulo-annular turns, in its central portion one or more helical turns and finally, in its distal portion, possibly one or several more annular turns.

According to another particular variant embodiment, the abovementioned structure reinforcing means comprise at least one link or several links between adjacent zigzags or bends, for example of successive terms of the stent.

According to another particular variant embodiment of the stent, at least some of the adjacent bends or zigzags of successive turns, in particular not only in the proximal portion but also in the central portion or in the distal portion, are provided with link arms intended to ensure continuity of the device from one end to the other.

According to a particular embodiment of this stent or endoprosthesis, the latter is made of a medically compatible metal or alloy, in particular a metal or alloy with shape memory such as nitinol, or a cobalt-based metal or a cobalt-based alloy, or a medically compatible steel such as 316L steel.

According to another particular variant embodiment, this stent may be coated with at least one coating layer that improves its biocompatibility and/or its deformability, and/or improves its mechanical resistance while reducing the risk of restenosis, and may, for example, have the structure as described in the applicant's prior application EP-A-1 674 817.

According to a particular embodiment, the abovementioned device is characterized in that it comprises a stent comprising several filament elements with bends or zigzags in the form of successive annular turns, at least some of which adjacent bends or zigzags are provided with at least one link arm intended to ensure continuity of the device from one end to the other.

According to a second aspect, the present invention also targets a method of implanting the implantable medical device or an angioplasty method, comprising:

a) the provision of at least one implantable medical device or endoprosthesis as described previously;

b) the provision of at least one dilating catheter on the balloon of which is mounted said implantable medical device;

c) the provision of at least one delivery catheter or guide catheter in which the dilating catheter is inserted;

d) the provision of at least one main guide or guide wire, and at least one secondary guide or guide wire, said main guide wire being provided for implantation in the main branch of a branching of a blood vessel, which comprises at least one stenosis to be treated, the secondary guide or guide wire being intended to be implanted in the secondary branch of said blood vessel, in which there is no restenosis to be treated, said stenosis to be treated being situated in immediate proximity to the branching of said blood vessel, called an ostial lesion;

e) using said guide catheter and the dilating catheter, on the one hand, the fitting of the implantable medical device in the vicinity of the branching of the blood vessel whose main branch includes the stenosis to be treated, and on the other hand the fitting of each of the two respectively main and secondary guides being careful to ensure that the main guide guiding the implantable medical device penetrates into the main branch and that the secondary guide penetrates into the secondary branch of the branching of the blood vessel;

f) the precise fitting of the implantable medical device at the branching itself, by exerting a push on the main guide or guide wire toward the distal end, the secondary guide or guide wire forming a stop abutment against the edge of the branching of the blood vessel;

g) the deployment of the implantable medical device to apply it firmly against the wall of the blood vessel including the ostial stenosis;

f) finally, after deployment of the implantable medical device, the dilating catheter or the fitting system is first removed; then, the respectively secondary and main guides or guide wires and finally the guide catheter are removed.

It will be understood that, by virtue of the invention as previously described and as resulting from the following description given with reference to an embodiment currently considered to constitute the best embodiment of the invention, the technical problems described previously are resolved and all the technical effects described previously or as resulting from the following description, and everything that those skilled in the art can deduce therefrom by themselves, given simply as an illustration, are obtained.

Other aims, features and advantages of the invention will become clearly apparent in light of the following explanatory description, given with reference to an embodiment currently considered to constitute the best embodiment of the invention, given simply as an illustration and which does not in any way limit the scope of the invention.

Figure 1:
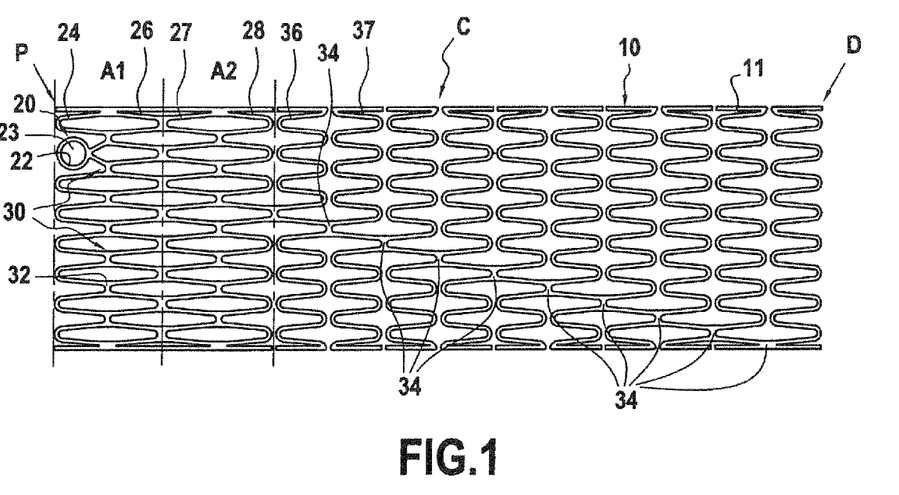
FIG. 1 represents, schematically and highly enlarged for better understanding, an implantable medical device 10 according to the invention, according to an embodiment considered to constitute the best embodiment of the invention, comprising an endoprosthesis, in this case, a stent 11 for example, the proximal end of which is provided with at least one means 20 of positioning the implantable device 10.

Referring to the figures, in particular FIG. 1, it can be seen that an implantable medical device according to the invention is represented by the general reference number 10, and the latter comprises a proximal end P, a distal end D and a central portion C.

At its proximal end P, this implantable medical device is characterized, according to the invention, in that it comprises at least one means 20 of positioning the medical device, in this case a stent 11, at a precise point of the branching E of a blood vessel V, such as a coronary artery.

Figure 3:
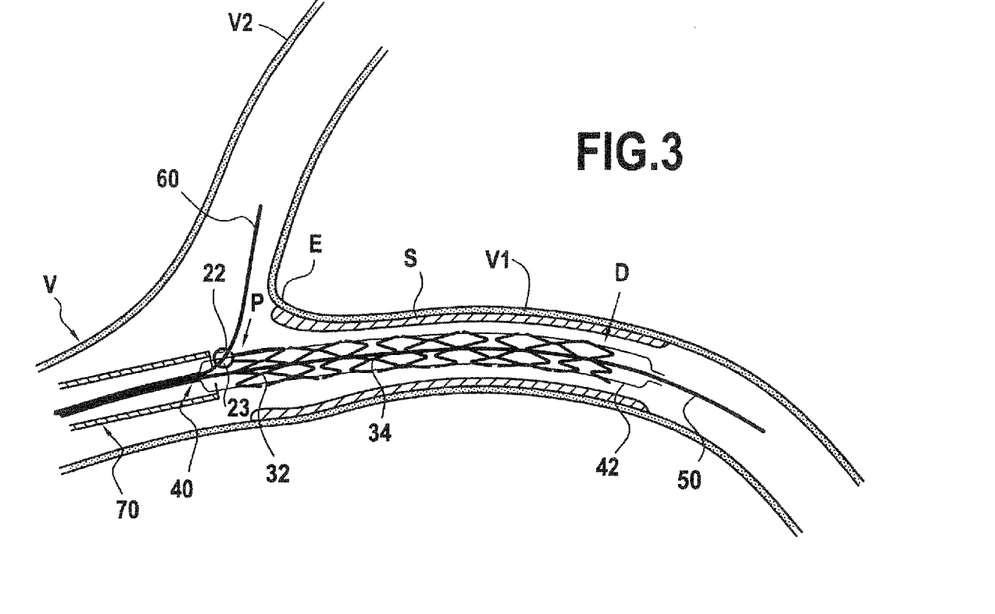
FIG. 3 represents a first step for fitting the implantable medical device using a delivery system comprising the guide catheter and the dilating catheter represented in FIG. 2, and in the vicinity of a branching E of a blood vessel V, in this case a coronary artery, at a lesion called an ostial stenosis, with prepositioning of the implantable medical device, in this case a stent, in the main or mother artery including the ostial lesion, with, also, the guide or guide wire mainly positioned in the main mother artery; and the secondary guide or guide wire positioned in the secondary artery or daughter artery.
Figure 4:
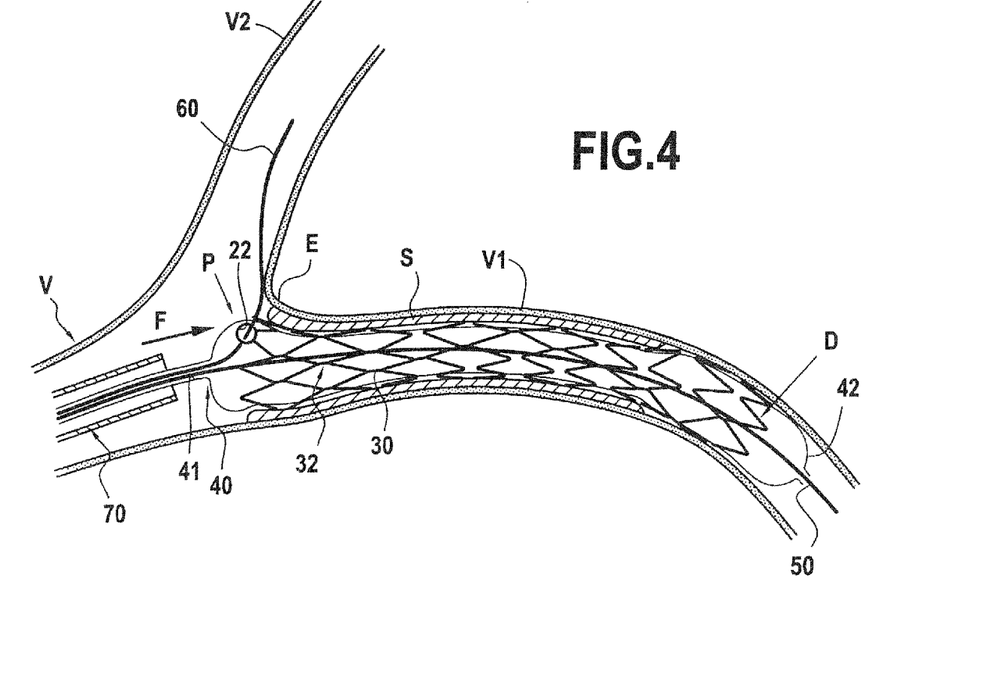
FIG. 4 represents the implantable medical device 10 implanted in its precise final position, after dilation, positioned exactly at the edge of the branching E by virtue of the secondary guide or guide wire 60 providing blockage against any further pushing forward of the medical device 10, in this case a stent 11.

According to a particular embodiment of the invention, this precise positioning means 20 comprises at least one closed mesh 22, defining a closed orifice 23, allowing for the passage of a guide or guide wire, such as the secondary guide or guide wire 60 as can be clearly seen in FIGS. 3 and 4.

According to another particular variant embodiment of the invention, the precise positioning means 20 comprises at least one closed mesh 22 defining an orifice 23, in this case of circular or ring form, produced at said proximal end as can be clearly seen notably in FIG. 1.

According to a particular embodiment of the invention, the implantable medical device 10 comprises or consists of a stent 11.

This stent 11 may be of any form as described in the prior art. For example, it could be of the type described in the applicant's prior document EP 0 969 779 B1, or of the type of that described in the document EP A 674 117, also by the applicant.

In a particular variant embodiment, the device 10 comprises, at least at the proximal end P, reinforcing means 30 intended to reinforce the structure of the stent 11, to avoid any undesirable significant deformation of the stent in an axial thrust exerted for the precise fitting of the latter inside the blood vessel V to be treated.

According to the currently preferred embodiment, as represented in FIGS. 1 to 4, the implantable medical device 10 comprises one or more filament-type elements such as 24, 26; 27, 28; 36, 37, etc., shaped with bends or zigzags, either in the form of annular turns as represented and clearly visible in the figures, or in the form of helical turns (not represented), or even a combination of the two (not represented).

These reinforcing means 30 can, according to a particular variant embodiment, comprise at least one link or several links 32, between successive zigzags or bends of the proximal end P, for example defined here by two successive turns 24, 26 of the filament element together forming a ring A1; the next ring A2 is similarly formed by two successive turns 27, 28 while the next ring will be formed by two other successive turns such as 36, 37, etc. It will be understood that the successive turns between successive rings are also attached by particular reinforcing means 30 comprising links 32. Beyond the proximal end P, at least some of the adjacent bends or zigzags, notably of successive turns such as 28, 36; 36, 37, etc., are provided with link arms such as 34 intended to ensure continuity of the device from one end to the other as can be clearly seen in particular in FIG. 1.

According to another particular variant embodiment, these reinforcing elements are present on all or almost all adjacent bends of the proximal end, whereas, beyond the proximal end, only certain adjacent bends or zigzags include link arms 34, in order to improve the flexibility and the deformation capability of the stent when it is fitted, by in this case reinforcing the effectiveness of the treatment of the stenosis.

According to another particular embodiment of the invention, the implantable medical device comprises a stent comprising or formed by at least one metal or metal alloy, for example formed by a nitinol-based alloy, or formed by a cobalt-based metal or a cobalt-based alloy, in particular a cobalt-chrome alloy, or, finally, made of 316L-type medical steel.

This stent can also be coated with at least one layer intended either to improve the biocompatibility and/or the anti-restenosis properties of the implantable medical device, and/or its anti-thrombosis properties, for example a stent as described in the applicant's prior application EP A 674 117.

According to another particular variant embodiment, it is also possible to provide for the presence of a medicine or a pharmaceutical molecule on the endoprosthesis-forming implantable medical device.

By virtue of these implantable medical devices, it is possible to implement the treatment or endoplasty method described previously, as shown in FIGS. 2 to 4.

Figure 2:
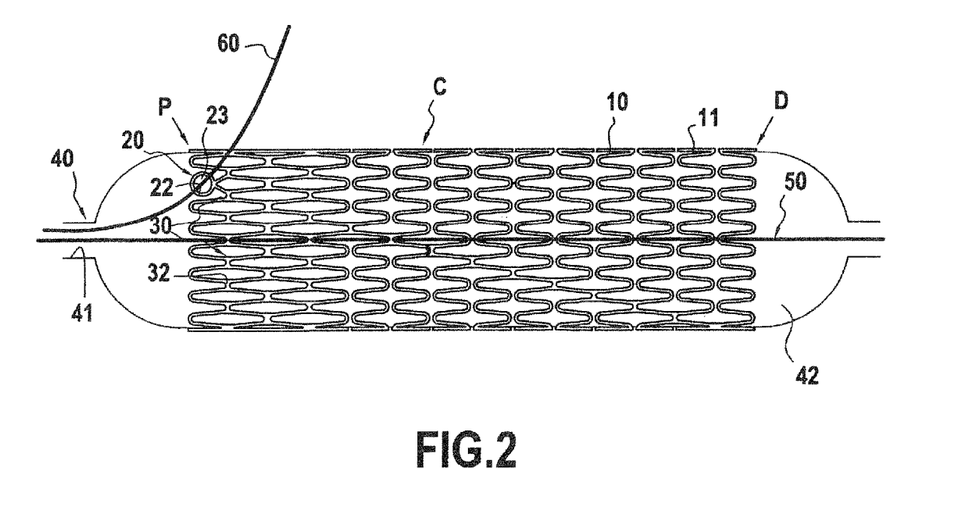
FIG. 2 represents an implantable medical device of FIG. 1 in position on a carrier catheter, comprising, at its distal end, a balloon for dilating said device, and inserted inside a guide catheter.

According to another variant and with reference to FIG. 2, the positioning of the implantable medical device 10, such as a stent 11, on a dilating catheter 40 with inflatable balloon 42 used to dilate the implantable medical device 10, in this case in the form of a stent 11 that can be deployed between a folded position as represented in FIG. 1 and FIG. 3, and a dilated position as represented in FIG. 4, has been shown.

As known to those skilled in the art, this dilating catheter 40 with balloon 42 comprises a hollow central portion or internal passage 41 allowing for the passage of a main guide or guide wire such as the main guide wire 50 represented in FIGS. 3 and 4, and in FIG. 2; and the secondary guide or guide wire 60 which will be provided to be prepositioned to pass into the positioning means 20, such as a closed or ring-shaped mesh 22. As is also known to those skilled in the art, the dilating catheter 40 with balloon 42 is itself arranged inside a guide catheter 70 to be inserted as far as the branching E of the blood vessel V to be treated.

It will be understood that the fitting of implantable medical devices such as a stent 11 is done according to the treatment or angioplasty method described previously. In particular:

the first fitting step is represented in FIG. 3, in which can be seen a branching E of a blood vessel V, for example, in this case, a coronary artery, comprising a main branch V1 which has a stenosis S which begins at the edge of the branching E itself, as can be clearly seen in FIG. 3 or 4.

As observed with reference to FIG. 3, the implantable medical device 10, such as, in this case, a stent 11, in the folded state, and therefore not dilated, is fitted at the branching of the blood vessel, while being positioned in the main branch V1, in this case a main or mother artery, which includes the stenosis S to be treated using the main guide or guide wire 50, whereas the secondary guide or guide wire 60 is positioned correctly in the secondary branching V2 of the blood vessel, in this case a secondary or daughter artery in the case of a coronary artery.

In FIG. 4, it can be seen that the second fitting step comprises a push according to the arrow F in the axial direction at the branching, toward the distal end D of the implantable medical device 10 such as a stent 11, the forward displacement movement of the implantable device 10 such as a stent 11 is stopped or blocked by virtue of the presence of the secondary guide or guide wire 60 immobilized in position against the edge of the branching E of the secondary branch V2, or daughter artery in the case of a coronary artery, as represented in FIG. 4 and clearly understandable to those skilled in the art.

It will be understood that, with the invention, a precise, exact and almost perfect positioning of the implantable medical device 10 such as a stent 11 is obtained at the branching E of the blood vessel V to be treated, in order to treat the lesions or ostial stenoses that have been difficult to treat hitherto.

Figure 5:
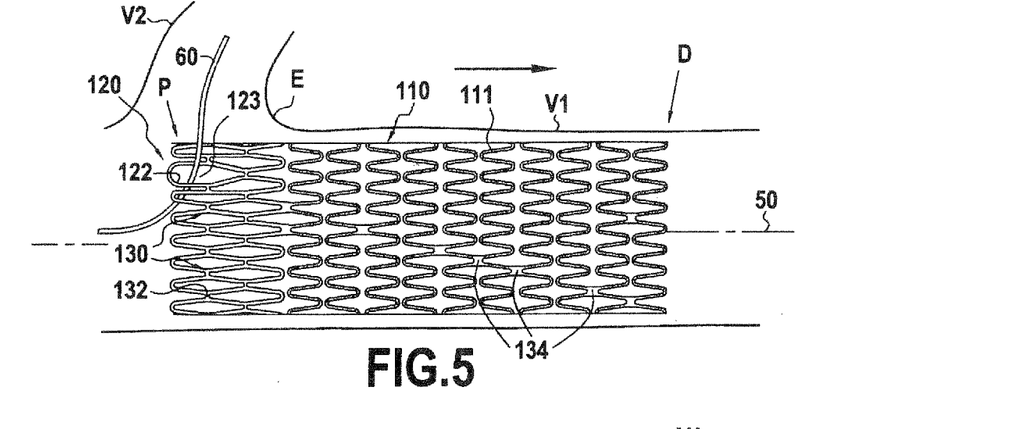
FIG. 5 represents a second embodiment of an implantable medical device 110 comprising a second embodiment of a positioning means 120, in this case in the form of a closed mesh, of substantially oblong or elongate form, of a size greater than the end meshes of the implantable medical device 110, in this case a stent, defining an internal orifice 123, in the fitting position at the branching E by virtue of the secondary guide or guide wire 60 providing a blockage against any further pushing forward of the medical device 110, in this, case a stent 111.

Referring to FIG. 5, this shows a second embodiment of a device according to the invention represented by the general reference number 110, such as a stent 111, comprising, at its proximal end, at least one positioning means 120 comprising at least one closed mesh 122, defining an orifice 123 for the passage of a guide or guide wire such as 60 intended to be implanted in a secondary branch V2 of the branching E of the blood vessel V1, V2. In the embodiment represented in FIG. 5, the closed mesh here has an oblong form, defining an orifice 123 of a much bigger size than the other orifices defined by other meshes of the proximal end P, in order to facilitate the identification of said orifice by, and the passage of, the guide wire 60. It will be understood here that the closed mesh such as 122 may have different forms and various dimensions to allow for the easy passage of the guide wire 60.

Figure 6:
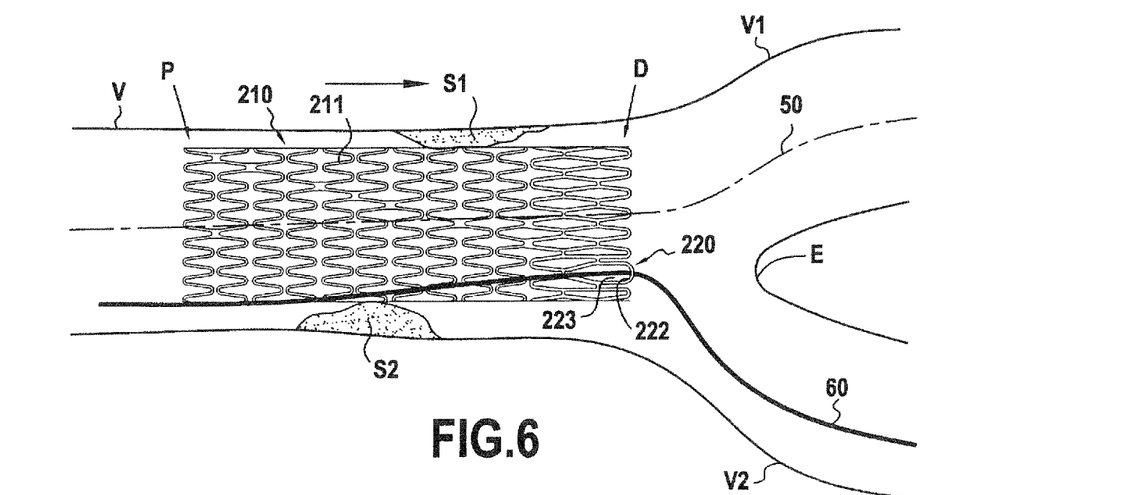
FIG. 6 represents a third embodiment of an implantable medical device according to the invention, referenced 210, implanted in its precise final position, upstream of a branching E, by virtue of the presence of a means of positioning the implantable device 220 at its distal end, while observing that, by reversing the implantable medical device 210, the proximal end and the distal end may be interchangeable, although particular stents may be provided for which the reversal is not required.

Referring to FIG. 6, this shows a third embodiment of an implantable medical device according to the invention represented by the general reference number 210. Here, the positioning means 220 comprises a closed mesh 222 defining an orifice 223, arranged at the distal end. By comparing the embodiments of FIGS. 5 and 6, it will be understood that, in most cases, the proximal end and the distal end are interchangeable, by simple reverse positioning of the implantable medical device. There may, however, be provided a clearly fixed proximal position and also a clearly fixed distal end allowing reversal only in exceptional cases.

It will be understood that, when the positioning device 210 comprises a closed mesh 220 in the distal position as represented in FIG. 6, this enables a new positioning of the implantable medical device 210 such as a stent, upstream of the branching E in the particular, but not exceptional, case of stenosis such as S1, S2 present upstream of the branching E, as shown in FIG. 6.

Figure 7:
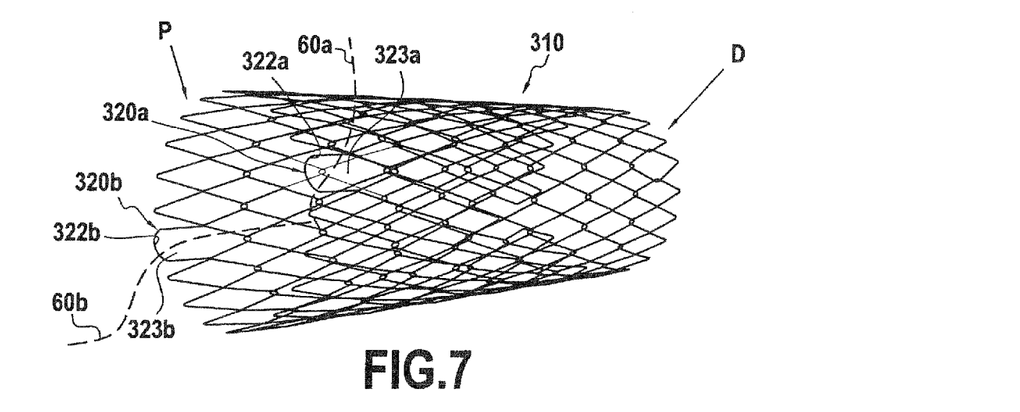
FIG. 7 represents another embodiment of an implantable medical device according to the invention, referenced 310, in which there are provided at least two closed meshes, respectively 320a, 320b, in this case, for example, arranged diametrically opposite, in the proximal portion P; this embodiment may also be applicable to the distal end portion, thus enabling the passage of two secondary guides or guide wires 60a to 60b, as shown in FIG. 8 which is described below.

Referring to FIG. 7, this shows a fourth embodiment of an implantable medical device according to the invention represented by the general reference number 310, comprising at least one positioning means 320a, 320b, in this case two positioning means 320a and 320b, at the proximal end P, but which could also be at the distal end D, also noting that the proximal and distal ends may be swapped or reversed. In the context of this embodiment of FIG. 7, the presence of at least two positioning means 320a, 320b is represented, said positioning means being arranged substantially diametrically opposite on the proximal end P. Here, the positioning means 320a and 320b comprise a closed mesh 322a, 322b which defines an internal orifice 323a, 323b, respectively, allowing for the passage of a guide or guide wire 60a, 60b, respectively.

It will be noted that, as in the case of the embodiment of FIG. 5, the closed mesh 323a, 323b is of a much larger size than the other meshes of the proximal portion in which it is inserted, in order to facilitate the identification of the orifice 323a, 323b and the introduction of the guide or guide wire 60a and 60b into said orifice 323a, 323b. For this, the mesh 323a, 323b may have a flared end, as can be clearly seen in FIG. 7.

Figure 8:
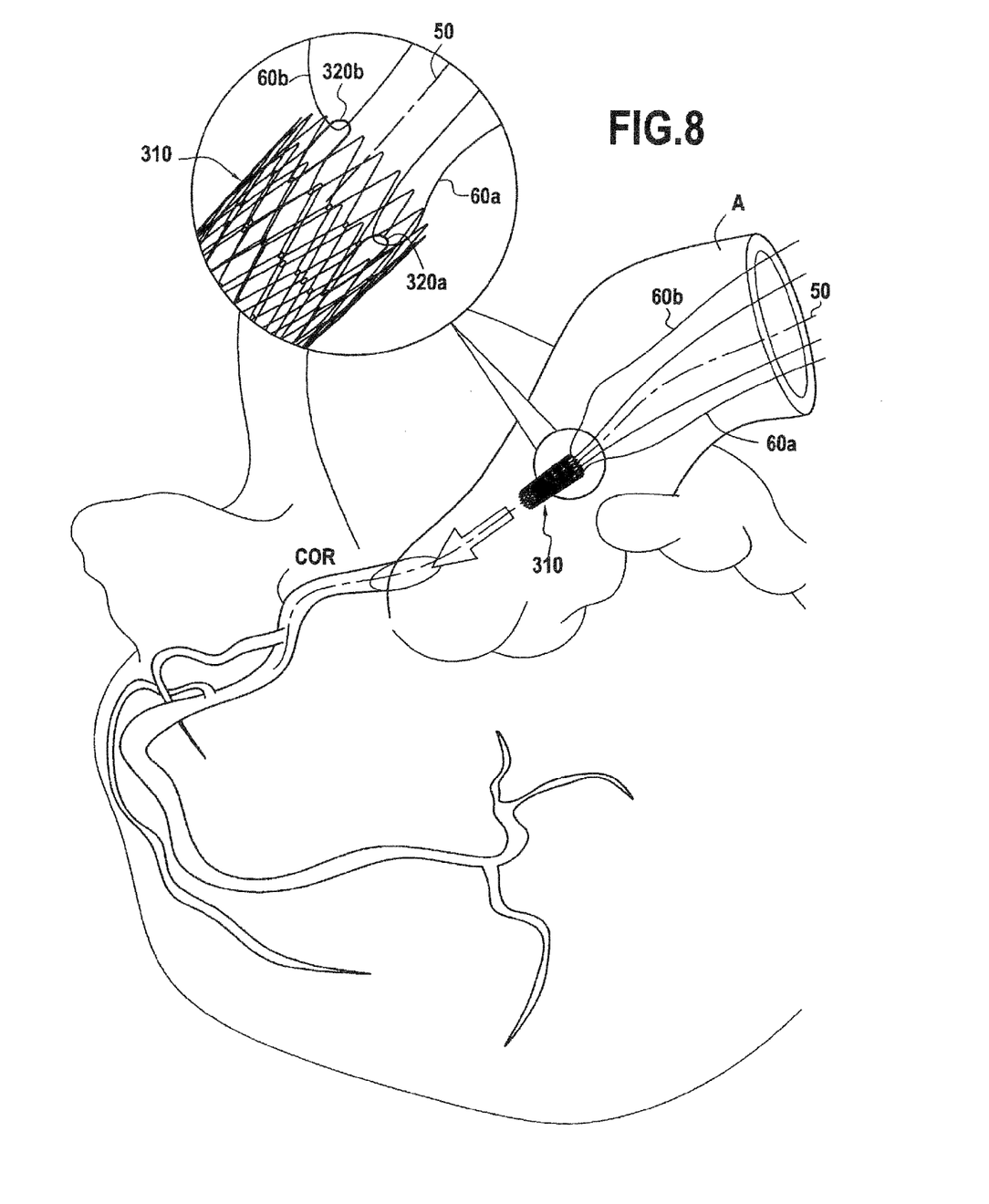
FIG. 8 represents a schematic general view of implantation of an implantable medical device 310 as represented in FIG. 7, showing an implantation by passage in the aorta A to precisely reach the ostium of the right coronary artery COR, as can be seen in FIG. 8, or even that of the left coronary artery. It will be noted that the use of two diametrically opposite meshes, combined with two secondary guides 60a and 60b, allows for precise and balanced positioning against the access edge to the secondary vessel, in this case the right coronary artery. Obviously, the invention could not be limited to the right coronary artery, given that the invention may be applicable to the insertion into any blood vessel, artery or coronary artery, in particular right or left.

Referring to FIG. 8, this diagrammatically shows the insertion of the implantable medical device 310 represented in FIG. 7, passing through the aorta A, at the precise level of the ostium of the right coronary artery COR, as represented, or even that of the left coronary artery. FIG. 8 diagrammatically shows the guide wires 60a, 60b inserted into the respective meshes 322a, 322b by passaging into the orifice 323a, 323b, which thus allows for the immobilizing of the stent at the ostium.

It will be understood here that, by displacement of the implantable medical device 310 mounted on a catheter in a manner that is conventional to those skilled in the art, on a main guide wire 50, the implantable medical device 310 is correctly inserted into the coronary artery in order to treat a stenosis, as is well known to those skilled in the art.

Figure 9:
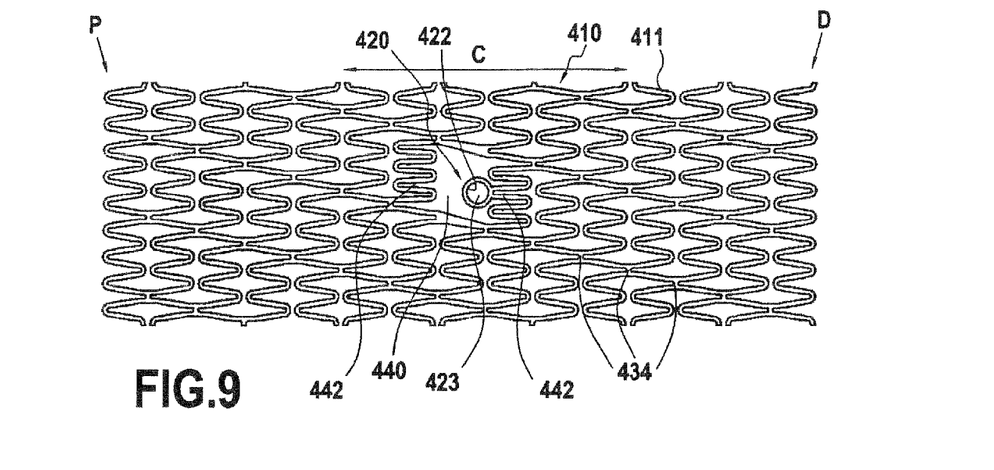
FIG. 9 represents yet another embodiment of an implantable medical device according to the present invention, referenced 410, in which there is provided at least one closed mesh 420 in the central portion C, this embodiment also being able to be combined with the preceding embodiments comprising at least one positioning means at the proximal end and/or at the distal end.

Referring to FIG. 9, this shows a fourth embodiment of an implantable medical device according to the invention represented by the general reference number 410 (the reference numerals are increased by 100 for each successive embodiment), in this case, for example, a stent 411, comprising a proximal portion P, a distal portion D and a central portion C. As for the preceding embodiments, the implantable medical device 410 comprises at least one positioning means 420 in this case comprising at least one closed mesh 422 of circular or ring form, in this case produced in the central portion C, for example substantially in the middle of the implantable medical device 410. As for the preceding embodiments, the closed mesh 422, which in this case is preferably unique, in the central portion C, defines an internal orifice 423 which allows for the passage of a secondary guide wire such as the guide wire 60 represented in FIGS. 10 and 11 below.

Figure 10:
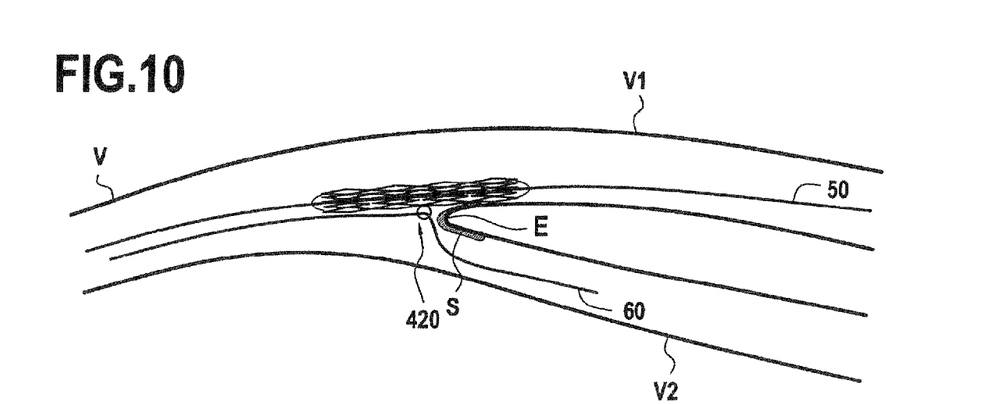
FIG. 10 represents the implantable medical device represented in FIG. 9 in position at the branching E of a blood vessel V.
Figure 11:
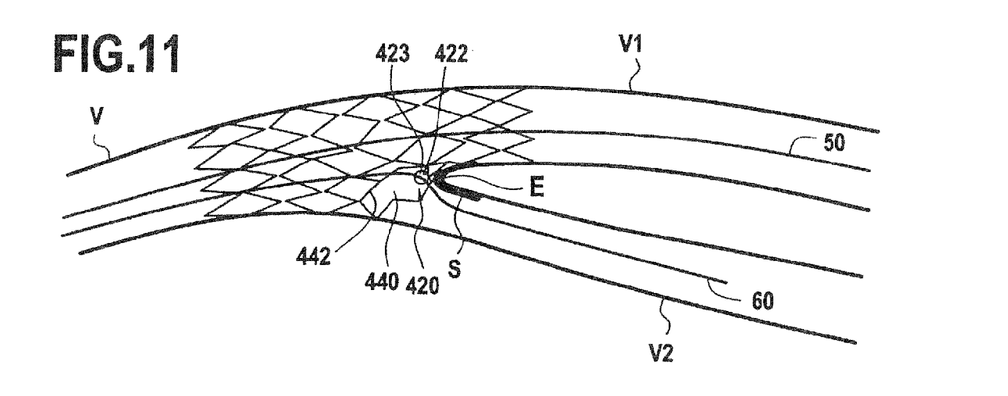
FIG. 11 represents the implantable medical device of FIGS. 9 and 10, according to the invention 410, in this case a stent, in the deployed state, according to which the lateral opening 440 has a dimension in the deployed state corresponding at least substantially to the diameter of the secondary vessel V2, the edge of which is delimited by specifically dedicated meshes 442 which, in the non-deployed state as represented in FIG. 9, have an accordion-shaped tighter design, so as to provide a greater deployment capability than the other meshes of the implantable medical device such as a stent 411.

In this embodiment of FIGS. 9 to 11, the positioning means 420 may form a protrusion of dedicated meshes 442 of the device 410 such as a stent 411, which are separated sufficiently to define an essentially central opening 440 allowing, in the deployed state, as represented in FIG. 11, the unobstructed passage into the secondary vessel V2, in other words, the size of the opening 440 in the deployed state of the implantable medical device 410 such as a stent 411, corresponds substantially to the diameter of the secondary vessel V2, as can be clearly seen in FIG. 11. Thus, these dedicated meshes 442 allow for a wider deployment than in the context of the other meshes i.e. those of the stent 411.

It will be understood that this embodiment may be combined with the preceding embodiments and, because of this, the positioning means of the implantable device 410 may comprise at least one closed mesh 422 defining an orifice 423 for the passage of a guide or a guide wire 60 produced in both the central portion and at at least one out of the proximal end P and the distal end D. At this proximal end and/or at the distal end, there may also be provided at least two closed meshes, for example arranged diametrically opposite as represented in certain embodiments of the preceding figures.

Referring to FIG. 10, this shows an implantable medical device 410 prepositioned at the branching E of a blood vessel V, being subdivided into a main vessel V1 and secondary vessel V2. The fitting of the implantable medical device 410 is done as for the preceding embodiments, and is well known to those skilled in the art, by virtue of a main guide wire 50, whereas the precise positioning of the device 410 takes place by virtue of the positioning device 420, in this case comprising a closed mesh 422 into which passes a dedicated secondary guide wire 60. This secondary guide wire 60 may be arranged outside the implantable medical device 410 such as a stent 411, or else inside the implantable medical device as is schematically represented in FIG. 11.

FIG. 11 shows the implantable medical device of FIGS. 9 and 10, in the deployed state. FIG. 11 also shows that the opening 440 is of a diameter substantially equal to the diameter of the secondary vessel V2.

Thus, the embodiment of the implantable medical device 410 of FIGS. 9 to 11 also makes it possible to address a different positioning of the implantable device 410.

The presence of the closed mesh 422 also makes it possible to adjust the medical device 410 such as a stent 411 to position it in the correct position with respect to the secondary vessel V2

It will be understood that these implantable medical devices according to the invention allow for a much greater versatility than with the implantable medical devices of the prior art.

The invention therefore provides a very significant and unexpected technical improvement for those skilled in the art.

The drawings that complement the description form an integral part of the invention.

The invention claimed is:

1. An implantable medical device to be implanted at an implantation site, the implantable device having a substantially, radially expandable or deployable cylindrical body with a circumferential surface and defining a longitudinal axis, and comprising a proximal end, a central portion and a distal end, said implantable device being radially expandable or deployable between an unexpanded or undeployed position and an expanded or deployed position, said implantable device having a precise positioning means at at least one of the proximal end, and the distal end, said precise positioning means for positioning the implantable device at a precise point of a branching of a blood vessel, said precise positioning means consisting of one or two closed guide wire loops of a size adapted for the precise passage of a secondary guide or guide wire to be introduced into a secondary branch of said branching of the blood vessel, a main branch of which is reached by a stenosis to be treated, and said one or two closed guide wire loops are substantially located within the circumferential surface at least in said unexpanded or undeployed position; the one or two closed guide wire loops adapted to be located away from a main blood vessel surface in the expanded or deployed position.

2. The device as claimed in claim 1, comprising two closed guide wire loops.

3. The device as claimed in claim 2, wherein the two closed guide wire loops are located substantially diametrically opposite.

4. The device as claimed in claim 1, wherein said device further comprises at least one lateral opening in the central portion and having a precise positioning means, the precise positioning means consisting of one or two closed guide wire loops located on an edge of the lateral opening and extending within a portion of the surface of the lateral opening and further substantially located within the circumferential surface both in said unexpanded or undeployed position and in said expanded or deployed position.

5. The device as claimed in claim 1, further comprising reinforcing means for reinforcing the device structure, thereby resulting in no substantial deformation of the implantable medical device when using a guide or guide wire exerting an action on at least one of the proximal end, of the distal end and of the central portion.

6. The device as claimed in claim 1, which consists essentially of a stent or endoprosthesis comprising one or more filament elements configured with bends or zigzags, resulting in a form selected from an annular turn form, an helical turn form, and a combination of both.

7. The device as claimed in claim 6, further comprising structure reinforcing means comprising one link or several links between successive zigzags or bends of the proximal end (P) of the stent or endoprosthesis.

8. The device as claimed in claim 6, wherein at least some of the adjacent bends or zigzags of successive turns are provided with one or several link arms ensuring continuity of the device from the proximal end to the distal end.

9. The device as claimed in claim 1, wherein said device is produced in a medically compatible metal or alloy.

10. The device as claimed in claim 9, wherein said medically compatible metal or alloy is selected from the group consisting of nitinol, a cobalt-based metal or a cobalt-based alloy, a medically compatible steel, and a 316L steel.

11. The device as claimed in claim 1, wherein the device is essentially consisting of a stent coated with at least one coating layer that improves at least one property selected from its biocompatibility, its deformability, its mechanical resistance, and reducing the risk of restenosis.

12. The device as claimed in claim 1, wherein the device is essentially consisting of a stent comprising several filament elements with bends or zigzags in the form of successive annular turns, at least some of which adjacent bends or zigzags are provided with one or several link arm(s) ensuring continuity of the device from the proximal end to the distal end.

13. The implantable medical device of claim 1, wherein the one or two closed guide wire loops comprises a shape selected from a circular shape, a ring shape, and an oblong or elongated shape.

14. An implantable medical device to be implanted at an implantation site, the implantable device having a substantially, aradially expandable or deployable cylindrical body having a circumferential surface and defining a longitudinal axis, comprising a proximal end, a central portion and a distal end, said implantable device being radially expandable or deployable between an unexpanded or undeployed position and an expanded or deployed position, said implantable device having a precise positioning means at the proximal end, said precise positioning means for positioning the implantable device at a precise point of a branching of a blood vessel, said precise positioning means consisting of one or two closed guide wire loops of a size adapted for the passage of a secondary guide or guide wire to be introduced into a secondary branch of said branching of the blood vessel, a main branch of which is reached by a stenosis to be treated, and     said one or two closed guide wire loops are substantially located within the circumferential surface at least in said unexpanded or undeployed position; the one or two closed guide wire loops adapted to be located away from a main blood vessel surface in the expanded or deployed position.

15. An implantable medical device to be implanted at an implantation site, said implantable device having a substantially, radially expandable or deployable cylindrical body with a circumferential surface and defining a longitudinal axis, comprising a proximal end, a central portion and a distal end, said implantable device being radially expandable or deployable between an unexpanded or undeployed position and an expanded or deployed position, said implantable device having a precise positioning means at the distal end, said precise positioning means for positioning the implantable device at a precise point of a branching of a blood vessel, said precise positioning means consisting of one or two closed guide wire loops of a size adapted for the passage of a secondary guide or guide wire to be introduced into a secondary branch of said branching of the blood vessel, a main branch of which is reached by a stenosis to be treated,     and said one or two closed guide wire loops are substantially located within the circumferential surface at least in said unexpanded or undeployed position; the one or two closed guide wire loops adapted to be located away from a main blood vessel surface in the expanded or deployed position.

16. The device as claimed in claim 5, comprising two closed guide wire loops.

17. The device as claimed in claim 16, wherein the two closed guide wire loops are located substantially diametrically opposite.

18. An implantable medical device to be implanted at an implantation site, the implantable device having a substantially, radially expandable or deployable cylindrical body having a circumferential surface and defining a longitudinal axis and comprising a proximal end, a central portion and a distal end, said implantable device being radially expandable or deployable between an unexpanded or undeployed position and an expanded or deployed position, said implantable device having at least one lateral opening located in the central portion, said at least one lateral opening having a precise positioning means located on an edge of the lateral opening and extending within a portion of the surface of the lateral opening, said precise positioning means for positioning the implantable device at a precise point of a branching of a blood vessel, said precise positioning means consisting of one or two closed guide wire loops of a size adapted for the passage of a secondary guide or guide wire intended to be introduced into a secondary branch of said branching of the blood vessel, a main branch of which is reached by a stenosis to be treated, and said one or two closed guide wire loops are substantially located within the circumferential surface both in said unexpanded or undeployed position and in said deployed or expanded position.

19. The implantable medical device of claim 18, wherein the one or two closed guide wire loops comprises a shape selected from a circular shape, a ring shape, and an oblong or elongated shape.

20. An angioplasty method of implanting the implantable medical device of claim 1, comprising:
    a) obtaining at least one said implantable medical device according to claim 1;
    b) mounting said implantable medical device on a balloon of at least one dilating catheter;
    c) inserting the dilating catheter in at least one delivery catheter or guide catheter;
    d) implanting in the main branch of a branching of a blood vessel at least one main guide or guide wire, and implanting in the secondary branch of the branching blood vessel at least one secondary guide or guide wire, said main branch comprising at least one stenosis to be treated, said stenosis to be treated being situated in immediate proximity to the branching of said blood vessel, called an ostial lesion;
    e) using said guide catheter and the dilating catheter, fitting of the implantable medical device in the vicinity of the branching of the blood vessel whose main branch includes the stenosis to be treated, and fitting of each of the two respectively main and secondary guides being careful to ensure that the main guide guiding the implantable medical device penetrates into the main branch and that the secondary guide penetrates through the closed guide wire loop into the secondary branch of the branching of the blood vessel;
    f) precisely fitting the implantable medical device at the branching itself, by exerting a push on the main guide or guide wire toward the distal end, the secondary guide or guide wire forming a stop abutment against the edge of the branching of the blood vessel;
    g) the deployment of the implantable medical device to apply it firmly against the wall of the blood vessel including the ostial stenosis; and
    h) first removing the dilating catheter or the fitting system; then, removing respectively the secondary and main guides or guide wires and finally removing the guide catheter.

* * * * *